United States Patent [19]
Satzinger et al.

[11] 4,231,933
[45] Nov. 4, 1980

[54] NOVEL 3-HYDROXY-PYRROLIN-2-ONE DERIVATIVES

[75] Inventors: Gerhard Satzinger, Denzlingen; Manfred F. Herrmann, St. Peter; Gustav Hechtfischer, Freiburg, all of Fed. Rep. of Germany

[73] Assignee: Warner-Lambert Company, Morris Plains, N.J.

[21] Appl. No.: 967,339

[22] Filed: Dec. 7, 1978

Related U.S. Application Data
[62] Division of Ser. No. 821,260, Aug. 3, 1977, abandoned.

[30] Foreign Application Priority Data

Aug. 14, 1976 [DE] Fed. Rep. of Germany ....... 2636722

[51] Int. Cl.$^3$ ................. C07D 207/12; C07D 401/04; C07D 407/04
[52] U.S. Cl. ............................ 260/326.5 FL; 546/281
[58] Field of Search ............... 260/326.5 FL; 546/281

[56] References Cited
PUBLICATIONS

Southwick et al., J. A. C. S., vol. 75, pp. 3413 to 3417, (1953).

Primary Examiner—Donald G. Daus
Assistant Examiner—David B. Springer
Attorney, Agent, or Firm—Stephen I. Miller; Stephen Raines; Albert H. Graddis

[57] ABSTRACT

The present invention is concerned with novel 3-hydroxy-pyrrolin-2-one derivatives and with the preparation thereof.

3 Claims, No Drawings

NOVEL 3-HYDROXY-PYRROLIN-2-ONE DERIVATIVES

This is a division of application Ser. No. 821,260 filed Aug. 3, 1977, abandoned.

The novel 3-hydroxy-pyrrolin-2-one derivatives according to the present invention are compounds of formula:

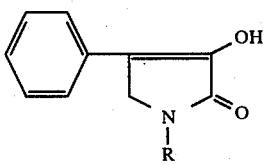

wherein R is a saturated or unsaturated, straight-chained or branched aliphatic hydrocarbon radical containing up to 6 carbon atoms or is the radical —Alk-Ar, in which Alk is an alkylene radical containing up to 3 carbon atoms and Ar is a phenyl or heteroaryl radical which may optionally carry halogen atoms and/or lower alkoxy radicals of less than 6 carbons.

Those compounds of general formula (I) are preferred in which R is a saturated or unsaturated aliphatic hydrocarbon containing up to 4 carbon atoms, Alk is a methylene, ethylene or propylene and Ar is a phenyl, furyl or pyridyl ring optionally substituted by a chlorine atom or a lower alkoxy radical.

The new compounds according to the present invention are valuable intermediates for the preparation of pharmacologically effective compounds which can be obtained by substitution of the 3-hydroxyl group. These substituted compounds are effective pharmaceuticals and can be used, for example, for the potential therapy of various forms of high blood pressure and of angiopathies and are the subject matter of U.S. Ser. No. 821,259 filed Aug. 3, 1977 (German Appln. Pat. No. 2636723.7)., now abandoned.

The present invention also provides a process for the preparation of compounds of formula (I) wherein a compound of the general formula:

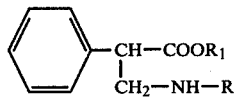

wherein R has the same meaning as above and $R_1$ is an alkyl radical, is condensed with a dialkyl oxalate in an anhydrous lower alcohol and in the presence of an alkali metal alcoholate at an elevated temperature.

The nature of the alkyl radical $R_1$ is not critical for the reaction and it may contain up to 8 carbon atoms. However, for economic reasons, lower alkyl esters (II) are preferred, such as the methyl, ethyl or isopropyl esters.

Lower alcohols which can be used include for example, methanol, ethanol, isopropanol, n-propanol and tert.-butanol.

By alkali metal alcoholate is meant the sodium or potassium compound corresponding to the lower alcohol used, sodium ethylate being preferred.

The condensation reaction is preferably carried out at a temperature of from 70° to 90° C.

The dialkyl oxalate is preferably a dialkyl ester containing up to 3 carbon atoms in each alkyl radical, diethyl oxalate being preferred.

The reaction according to the present invention is unexpected since it is known that oxalic acid diesters normally react with β-aminopropionic acid esters in a different manner (see J.A.C.S., 75, 3413/1953). Thus, for example, the condensation of methyl oxalate with methyl β-benzylaminopropionate in the presence of sodium methylate gives 4-carbomethoxy-1-benzyl-2,3-dioxopyrrolidine. It could not have been expected that the use of an anhydrous lower alcohol solvent would yield the 3-hydroxy-pyrrolin-2-ones of the present invention in yields of, in some cases, more than 90%.

The compounds of general formula (II) used as starting materials are either known ($R_1$=ethyl; R=n-butyl or benzyl; cf. J. Org. Chem., 35, 414/1970) or can be prepared without difficulty in the manner described therein by the reaction of appropriate amines with an atropic acid ester, for example ethyl atropate.

The following examples are given for the purpose of illustrating the present invention:

EXAMPLE 1

1-Methyl-3-hydroxy-4-phenyl-3-pyrrolin-2-one

A solution of sodium ethylate, prepared from 13.8 g. sodium and 300 ml. anhydrous ethanol, is mixed with 62.4 g. ethyl 2-phenyl-3-N-methylaminopropionate and 43.8 g. diethyl oxalate and heated under reflux for 45 minutes. The precipitated sodium salt is filtered off, taken up in water and the pyrrolinone compound precipitated out with 2 N hydrochloric acid. After filtering off with suction and washing with water, the product is dried and boiled in methanol. After separation and drying, there is obtained 40.0 g. (70% of theory) 1-methyl-3-hydroxy-4-phenyl-3-pyrrolin-2-one; m.p. 245°–250° C.

EXAMPLE 2

1-Ethyl-3-hydroxy-4-phenyl-3-pyrrolin-2-one 83.0 g. ethyl 2-phenyl-3-N-ethylaminopropionate and 55.0 g. diethyl oxalate are added to a solution of sodium ethylate, prepared from 17.5 g. sodium and 700 ml. anhydrous ethanol. The reaction mixture is heated under reflux for 45 minutes. The sodium salt began to precipitate out of solution after 15 minutes. The sodium salt is filtered off, taken up in water and the aqueous solution is clarified with infusorial earth and acidified with 2 N hydrochloric acid. The product thus obtained is washed with water and dried. There is obtained 56.0 g. (73% of theory) 1-ethyl-3-hydroxy-4-phenyl-3-pyrrolin-2-one; m.p. 192°–195° C., after recrystallization from ethanol.

EXAMPLE 3

1-n-Butyl-3-hydroxy-4-phenyl-3-pyrolin-2-one

A solution of sodium ethylate, prepared from 400 ml. anhydrous ethanol and 11.5 g. sodium, is mexed with 62.4 g. ethyl 2-phenyl-3-N-n-butylaminopropionate and 36.5 g. diethyl oxalate, and then heated under reflux for 90 minutes. The precipitated sodium salt is filtered off, taken up in water and the turbid solution obtained is clarified with infusorial earth. The pyrrolinone compound is precipitated out with dilute hydrochloric acid. The product thus obtained is filtered off with suction, washed with water, dried and recrystallized from isopropanol. There is obtained 36.0 g. (62% of theory) 1-n-butyl-3-hydroxy-4-phenyl-3-pyrrolin-2-one; m.p. 137°–139° C.

EXAMPLE 4

1-Allyl-3-hydroxy-4-phenyl-3-pyrrolin-2-one

A solution of sodium ethylate, prepared from 500 ml. anhydrous ethanol and 17.2 g. sodium, is mixed with 83.0 g. ethyl 2-phenyl-3-N-allylaminopropionate and 51.6 g. diethyl oxalate and heated under reflux for 30 minutes. After cooling, 2 liters of water are added with stirring. The remaining turbidity is removed by extraction with diethyl ether and the aqueous phase is acidified with 2 N hydrochloric acid. The precipitated product is separated, washed with water and dried. There is obtained 62.0 g. (77% of theory) 1-allyl-3-hydroxy-4-phenyl-3-pyrrolin-2-one; m.p. 178°–183° C., after recrystallization from isopropanol-methanol.

EXAMPLE 5

1-Benzyl-3-hydroxy-4-phenyl-3-pyrrolin-2-one 0.1 Mol (28.3 g.) ethyl 2-phenyl-3-N-benzylamino propionate and 0.1 Mol (14.6 g.) diethyl oxalate are mixed and introduced at ambient temperature into a solution of sodium ethylate, prepared from 300 cc. dry ethanol and 4.6 g sodium. The reaction mixture is heated under reflux for 30 minutes. The sodium salt obtained is filtered off, dissolved in water and acidified with 2 N hydrochloric acid. The precipitate obtained is filtered off with suction, dried and recrystallized from dimethyl formamide. There is obtained 15.3 g. (58% of theory) 1-benzyl-3-hydroxy-4-phenyl-3-pyrrolin-2-one; m.p. 235° C. (decomp.).

EXAMPLE 6

1-(4-Methoxybenzyl)-3-hydroxy-4-phenyl-3-pyrrolin-2-one

A solution of sodium ethylate, prepared from 9.2 g. sodium and 500 ml. anhydrous ethanol, is mixed with 62.6 g. ethyl 2-phenyl-3-N-(4-methoxybenzylamino)-propionate and 29.4 g. diethyl oxalate, and heated under reflux for 75 minutes. The precipitated sodium salt is taken up in water and acidified with 2 N hydrochloric acid. The crude product is washed with water and dried. There is obtained 54.0 g. (91% of theory) 1-(4-methoxybenzyl)-3-hydroxy-4-phenyl-3-pyrrolin-2-one; m.p. 195°–198° C., after recrystallization from ethylcellosolve.

EXAMPLE 7

1-(4-Chlorobenzyl)-3-hydroxy-4-phenyl-3-pyrrolin-2-ones

A solution of sodium ethylate, prepared from 400 ml. anhydrous ethanol and 11.5 g. sodium, is mixed with 79.5 g. ethyl 2-phenyl-3-N-(4-chlorobenzylamino)-propionate and 36.5 g. diethyl oxalate and heated under reflux for 30 minutes. The precipitated sodium salt is filtered off, stirred in water and acidified with 2 N hydrochloric acid. The product thus obtained is collected, washed with water and, after drying, boiled in isopropanol. There is obtained 51.0 g. (68% of theory) 1-(4-chlorobenzyl)-3-hydroxy-4-phenyl-3-pyrrolin-2-one; m.p. 187°–188° C. (decomp.), after recrystallization from ethanol.

EXAMPLE 8

1-(1-Phenethyl)-3-hydroxy-4-phenyl-3-pyrrolin-2-ones

A solution of sodium ethylate, prepared from 17.0 g. sodium and 500 ml. anhydrous ethanol, is mixed with 115.0 g. ethyl 2-phenyl-3-N-(1-phenethylamino)-propionate and 57.0 g. diethyl oxalate and heated under reflux for 3 hours. The precipitated sodium salt is filtered off and washed with diethyl ether. The product is taken up in water and acidified with dilute hydrochloric acid. The separated solid product is filtered off, washed with water, dried and recrystallized from ethyl acetate-ligroin. There is obtained 13.4 g. (12% of theory) 1-(1-phenethyl)-3-hydroxy-4-phenyl-3-pyrrolin-2-one; m.p. 151°–153° C.

EXAMPLE 9

1-(2-Phenethyl)-3-hydroxy-4-phenyl-3-pyrrolin-2-one

A solution of sodium ethylate, prepared from 600 ml. anhydrous ethanol and 13.8 g. sodium, is mixed with 100.0 g. ethyl 2-phenyl-3-N-(2-phenethylamino)-propionate and 44.0 g. diethyl oxalate and heated under reflux for 30 minutes. The reaction mixture is worked up in the manner described in Example 7. There is obtained 66 g. (79% of theory) 1-(2-phenethyl)-3-hydroxy-4-phenyl-3-pyrrolin-2-one; m.p. 192°–195° C.

EXAMPLE 10

1-Furfuryl-3-hydroxy-4-phenyl-3-pyrrolin-2-one

Into a solution of sodium ethylate, prepared from 200 ml. anhydrous ethanol and 10.4 g. sodium, there is added, while stirring, 61.0 g. ethyl 2-phenyl-3-N-furfurylaminopropionate and 32.0 g. diethyl oxalate. The reaction mixture is heated under reflux for 30 minutes. The precipitated sodium salt is taken up in water and worked up in the manner described in Example 8. There is obtained 27.0 g. (48% of theory) 1-furfuryl-3-hydroxy-4-phenyl-3-pyrrolin-2-one; m.p. 222°–226° C., after recrystallization from methylcellosolve.

EXAMPLE 11

1-(3-Picolyl)-3-hydroxy-4-phenyl-3-pyrrolin-2-one

Into a solution of sodium ethylate, prepared from 500 ml. anhydrous ethanol and 23.0 g. sodium, there is added 142.0 g. ethyl 2-phenyl-3-N-(3-picolylamino)-propionate and 73.0 g. diethyl oxalate. The reaction mixture is heated under reflux for 1 hour. The precipitated sodium salt is filtered off and taken up in water and the turbid solution obtained is extracted with diethyl ether. The aqueous phase is adjusted to pH 6 with dilute hydrochloric acid. The precipitated product is filtered off, washed and dried. There is obtained 69.0 g. (50% of theory) 1-(3-picolyl)-3-hydroxy-4-phenyl-3-pyrrolin-2-one; m.p. 205° C. (decomp.).

We claim:

1. A process for the preparation of compounds of the formula:

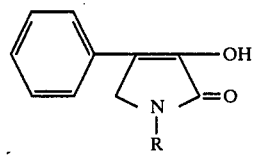

in which R is a saturated or unsaturated alkyl group of up to 6 carbon atoms or the group alk-ar, wherein alk is a methylene-, ethylene- or propylene- group and ar is a substituted or unsubstituted phenyl-, furyl-, or pyridyl-ring wherein the substituent is methoxy or chloro; wherein a compound of the formula:

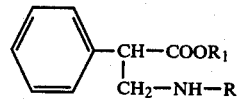

in which R has the above meaning and $R_1$ is an alkyl group of up to 8 carbon atoms, is condensed with a dialkyl oxalate of the formula:

$$\begin{array}{c} COOR_2 \\ | \\ COOR_2 \end{array}$$

in which $R_2$ is an alkyl group of up to 3 carbon atoms, in an anhydrous lower alcohol of up to 3 carbon atoms in the presence of a corresponding alkali metal alcoholate at a temperature in the range of 70° to 90° C.

2. Process according to claim 1, wherein the dialkyl oxalate used is diethyl oxalate.

3. Process according to claim 1, wherein the lower alcohol used is methanol, ethanol, isopropanol, n-propanol or tert.-butanol.

* * * * *